United States Patent
Malowaniec

(10) Patent No.: US 7,462,756 B2
(45) Date of Patent: Dec. 9, 2008

(54) SKIN-FRIENDLY SINGLE-USE PRODUCT

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 10/559,408

(22) PCT Filed: Jul. 8, 2004

(86) PCT No.: PCT/EP2004/007508

§ 371 (c)(1), (2), (4) Date: Dec. 5, 2005

(87) PCT Pub. No.: WO2005/004938

PCT Pub. Date: Jan. 20, 2005

(65) Prior Publication Data

US 2006/0129117 A1 Jun. 15, 2006

(30) Foreign Application Priority Data

Jul. 10, 2003 (EP) ................... 10331192

(51) Int. Cl.
*A61F 13/15* (2006.01)
*A61F 13/20* (2006.01)

(52) U.S. Cl. ............... 604/381; 604/367; 604/359

(58) Field of Classification Search ......... 604/359–360, 604/365–376, 381
See application file for complete search history.

(56) References Cited

U.S. PATENT DOCUMENTS

| 5,407,442 | A | * | 4/1995 | Karapasha | ........ 604/359 |
|---|---|---|---|---|---|
| 5,643,588 | A | | 7/1997 | Warner | |
| 6,387,495 | B1 | | 5/2002 | Lindon | |
| 2002/0120242 | A1 | | 8/2002 | Tyrrell | |
| 2002/0136755 | A1 | | 9/2002 | Tyrrell | |
| 2002/0150761 | A1 | | 10/2002 | Lange | |
| 2003/0100877 | A1 | | 5/2003 | Erdman | |
| 2003/0118394 | A1 | * | 6/2003 | King et al. | ........ 401/195 |
| 2003/0119394 | A1 | | 6/2003 | Hamman | |
| 2003/0120225 | A1 | * | 6/2003 | Everhart et al. | ........ 604/285 |

FOREIGN PATENT DOCUMENTS

| EP | 1 145 724 | | 10/2001 |
|---|---|---|---|
| EP | 1 250 940 | | 10/2002 |
| WO | 99/38541 | * | 8/1999 |
| WO | WO 02/36053 | | 5/2002 |
| WO | WO 03/043670 | | 5/2003 |
| WO | WO 03/053487 | | 7/2003 |

* cited by examiner

Primary Examiner—Michele Kidwell
(74) Attorney, Agent, or Firm—Paul Vincent

(57) ABSTRACT

The invention relates to a suction body component which is suitable for the durable storage of body fluids and is used to absorb, skin-friendly, single-use products. The suction body component comprises a carrier material and a particulate super absorbing polymer material. The super absorbing polymer material has a core provided with an outer surface and at least one part of the outer surface thereof comprises a coating agent which is used to reduce the absorption rate of the core of the super absorbing polymer material. The coating agent of the super absorbing polymer material comprises a skin-care product.

13 Claims, 1 Drawing Sheet

SKIN-FRIENDLY SINGLE-USE PRODUCT

BACKROUND OF THE INVENTION

This application is the national stage of PCT/EP2004/007508 filed On Jul. 08, 2004 and also claims Paris Convention priority of DE 103 31 192.0 filed on Jul. 10, 2003.

The present invention concerns an absorbing, skin-friendly, single-use product for receiving and storing, in particular, aqueous body liquids, containing a suction body component which is suited for long-term storage of body liquids and comprises a particulate super-absorbing polymer material containing a skin care product.

A large number of conventional diapers, incontinence diapers, sanitary towels, panty liners, dressing materials, and other single-use products for absorbing body liquids, conventionally comprise super-absorbing polymer materials (SAP). These materials (often also referred to as hydro gels, absorbing gels, hydrocolloids or simply as absorbing polymers) are suited for long-term capture of body liquids, such as urine, blood, menstruation blood, wound exudates or liquid stool while swelling and do so in amounts which exceed many times their own weight.

Single-use products having SAP can bind and-durably store large amounts of body liquid, but often with the consequence that the products are borne proximate to the body for a very long time. Due to the continuously moist climate, the skin flora and the plurality of partially very complex components contained in the above-mentioned body liquids, such as i.a. enzymes and other proteins, lipids and micro-organisms, a series of chemical and biochemical reactions and microbiological decompositions as well as disintegrating processes take place, which affect the skin of the user. This often causes dermatitis, eczema, skin irritation, and similar skin problems. Another unpleasant side effect is the generated odor, which is more unpleasant than that of the originally excreted body liquid.

There have been several attempts to counteract these effects.

WO-2002/051456-A2 describes e.g. the use of a diaper top sheet comprising a plant extract having skin-caring properties.

WO-96/16682-A1 concerns a nursing diaper, wherein the top sheet is provided with a lotion based on fatty substances. The lotion on the top sheet is initially immobile and should be transferred to the skin, in particular, through the body temperature.

WO-01/52913-A1 discloses absorbing hygiene articles with biologic precursors such as spurs or germ cells which, upon use of the diaper, turn into e.g. lactic acid-producing organisms, expel undesired micro-organisms, or develop antagonistic properties thereto.

WO-01/03749-A1 describes a hygiene article for children comprising an active plant substance containing *Sophorae flavescens*. Further components may be *Phellodendri Cortex, Artemisia folis, Dictamnus alpus* and *Dictamnus alum*.

WO-00/72891-A1 claims an absorbing hygiene article containing a drying agent. The drying agent is preferably a desiccant or humectant and is added to the hygiene article in order to obtain a relative air moisture on the skin of <85%.

The use of a bacterial staphylococcus aureus inhibitor to reduce the risk of toxic shock syndrome, consists of mono and die-esters of multivalent aliphatic alcohols and fatty acids as disclosed in EP-0395099-B1.

WO-02/42379-A1 discloses a formally defined SAP having the capacity to bind odors. The SAP preferably contains a plant component which positively influences binding of the odors.

DE-10257002-A1 describes foamy hydro gel containing skin care products.

EP-1051203-B1 describes an SAP which contains a 1-hydroxy-2-pyrrolidone-derivative as an antimicrobial substance. This substance is described as coating the absorbing polymer.

One must assume that, during use, the antimicrobial substance is dissolved immediately after wetting, and binding of the liquid, i.e. swelling of the absorbing polymer starts immediately. The prompt swelling inhibits and finally blocks mobility of the antimicrobial substance. This has the consequence that an insufficient amount of the antimicrobial substance reaches the skin of the user. Another disadvantage of an SAP with antimicrobial substance is its limited antimicrobial effectivity over a longer period of time.

It is therefore the underlying purpose of the present invention to provide a suction body component which comprises super-absorbing polymer material (SAP) and a skin-care product which reaches the skin of the user more readily and has increased effectivity over a longer period of time.

SUMMARY OF THE INVENTION

This object is achieved by a suction body component comprising a carrier material and a super-absorbing polymer material, wherein the super-absorbing polymer material comprises a core with an outer surface, wherein at least part of the outer surface of this core comprises a coating agent which reduces the absorption rate of the core of the super-absorbing polymer material, wherein at least the coating agent comprises a skin-care product.

Although the active mechanism is not yet completely clear, the advantages of the inventive suction body component, i.e. the positive effect on the health of the skin of the user of the single-use product, are probably due to the following dynamics.

After wetting of the inventive suction body component, the body liquid initially acts on the coating of the super-absorbing polymer material, which contains the skin-care product. The skin-care product is thereby released or otherwise activated, e.g. in that the coating agent is dissolved and/or swells in such a manner that the core of the super-absorbing polymer is exposed with delay, i.e. is subjected to the action of the body liquid at a later time. The absorption rate of the core of the super-absorbing polymer material is thereby reduced. A reduction in the absorption rate of the core of the super-absorbing polymer material changes the absorption behavior of the core such that, following liquid application, liquid absorption as a function of time is delayed, and/or the speed of liquid absorption (g liquid per unit time) is reduced, and/or the overall liquid absorption capacity (g liquid per g SAP of the core) is reduced.

The interaction between the body liquid and the coated super-absorbing polymer comprising the skin-care product consequently exhibits two optionally overlapping phases. The skin-care product contained in the coating can reach the skin in the first phase via the body liquid which has not been completely bound. Suitable transport mechanisms include e.g. diffusion and/or capillary action. Only at the start of the second phase is the amount of free body liquid and therefore the mobility of the skin-care product reduced due to absorption of the body liquid and its resulting immobilization by the core of the super-absorbing polymers, which is increasingly exposed by the coating agent.

In a preferred embodiment, the core of the super-absorbing polymer also contains a skin-care product. In this case, absorption of the body liquid, i.e. binding of the body liquid to the core of the super-absorbing polymer can be accompanied by binding chemical substances and/or micro-organisms and/or reacting them with the skin-care product of the core, to avoid danger to the skin due to the above-mentioned disintegration and decomposition reactions. This also involves, in particular, a bactericidal and/or microbicidal effect and may contain the same skin-care product as that of the coating agent. However, it is also feasible to use one or more further different skin-care products. In this case, it would be advantageous to select a skin-care product for the coating which is suited to release its skin-caring action through direct contact with the skin, whereas the above-described skin-care product of the core is suited to inhibit or decompose detrimental substances and/or micro-organisms.

Any means which has a direct or indirect positive influence on the health of the skin may be used as skin-care product. The skin-care products disclosed in DE-10257002-A2 are particularly advantageous. In this connection, reference is made to DE-10257002-A2, the entire disclosure of which is hereby incorporated by reference. Water-soluble means are particularly suited. Fat-soluble or amphoteric means are also feasible and advantageous. The following Table 1 contains an overview of substances which are particularly suited. Each individual substance is suited and advantageous as a skin-care product of an inventive suction body component. This also obtains for all possible combinations of the mentioned substances, in particular, those resulting from physical mixture and/or chemical reactions such as e.g. esterification of hydroxy compounds with fatty acids.

In addition to the plant extracts mentioned i.a. in Table 1, such as e.g. tea extract, in particular, green tea extract, the herb itself, i.e. the leaf material of the plant, in particular, of green tea, can also be used, with particular preference, in a correspondingly disintegrated form, e.g. as powder.

TABLE 1

| Substance/Substance Class/Extract | Effect/Protection | Solubility |
| --- | --- | --- |
| Vitamins and derivatives: | | |
| Vitamin A (retinol), (provitamin: beta-carotin) and derivatives with fatty acids such as e.g. retinyl palmitate | VG, EH: growth factor for epithelium cells, epithel protection, resistive factor, infection protection | Fat-soluble |
| Vitamin B complex: | | |
| B2 (Riboflavin) | VG, EH: cofactor FAD/FMIN for redox enzymes, antiphlogistic, general skin protection | H2O soluble (limited) |
| B6 (Pyridoxin/pyridosamin/pyridoxal) | VG, EH: cofactor for amino acid metabolism, inflammation protection | H2O soluble |
| Biotin (previously: Vitamin H) | VG: carboxylation reactions; "general" skin protection | Fat-soluble |
| Vitamin C (ascorbic acid) also as ester with fatty acids yields e.g. ascorbyl palmitate/-stearate | AO, VG: build-up of skin collagen, immune modulation | H2O soluble/fat-soluble |
| Vitamin E (alpha Tocopherol) also as derivative such as e.g. dioleyltocopheryl methyl silanol, Tocopheryl acetate/-linoleate/-nicotinate/-succinate/-oleate | AO, VG: important for electron transport; oxidative protection | Fat-soluble |
| Folic acid (tetrahydro folic acid) | VG: important for purine-/nucleotide metabolism, inflammation protection | H2O soluble |
| "Vitamin" F: see fatty acid; in particular, linolic, linolenic, and arachidonic acid | | |
| K (phylloquinone) | AO, VG: antihemorrhagic activity, antioxidative | Fat-soluble |
| Methyl methionine (previously: vitamin U) | VG: essential amino acid | H2O soluble |
| Niacin (nicotinic acid amide) | VG: cofactor NAD/NADP for redox reactions; inflammation protection; general skin protection | H2O soluble |
| Pantothenic acid (previously: vitamin B3) | VG: component of coenzyme A, inflammation protection | H2O soluble |
| Coenzyme Q 10 (ubiquinone) | AO, VG; electron transport, antioxidative | Fat soluble |
| Organic (fatty) acids: | | |
| Salicylic acid and alkyl esters thereof such as e.g. hexyl dodecyl salicylate | AO VG, EH: decomposition of hard skin, antiphlogistic | H2O soluble/Fat soluble |
| Short-chain, saturated and unsaturated fatty acids such as e.g. lactic, glyceric, malic, succinic acid, fumaric acid | VG: metabolic products, pH-regulators, | H2O soluble |

TABLE 1-continued

| Substance/Substance Class/Extract | Effect/Protection | Solubility |
|---|---|---|
| alpha lipoic acid | AO, VG: antioxidant | Fat soluble |
| Hyaluronic acid (fatty acid with sugar residue) | VG: mucopolysaccharide as "lubricant" | H2O soluble |
| Alpha hydroxy acids (AHA) such as e.g. glycolic acid and derivatives such as e.g. ethyl glycolate, | AO, VG: glycolic acid is an important metabolic product | H2O soluble/ Fat soluble |
| Arachidonic acid and fatty acid ester with e.g. propionic acid | AO, VG: essential fatty acid | Fat soluble |
| Long-chain, partially (multiply) unsaturated and branched fatty acids (see also fatty acids below) | Partially AO, VG: metabolic products | Fat soluble |
| Citric acid and derivatives: acetyl triethyl/tributyl/trihexyl/trioctyl citrate | VG. Metabolic product | H2O soluble |
| Fats/fatty acid esters/phosphates: | | |
| Glycerine and triglycerides (glycerine esterified with the fatty acids mentioned as examples herein) | VG: metoblic products and membrane/skin components | Fat soluble |
| Fatty acids (e.g. also as ammonium salts) such as e.g. palmitic-/stearic-/oleic-/linolic-/linolenic-/arachidonic-/behenic-/myristic-/capric-/castor acid | Partially AO, VG: metabolic products, components of skin fats | Fat soluble |
| Phosphatidyl choline ("lecithin") | VG: metabolic products, components of biological membranes | Amphoteric |
| Sphingolipids/-myelins | VG: metabolic products, components of biological membranes | Amphoteric |
| Ceramides/cerebrosides | VG: metabolic products, components of biological membranes | Amphoteric |
| Lanolin/acetylated lanolin alcohol and derivatives with fatty acids | VG: metabolic product of animals | Fat soluble |
| Aluminium stearate/distearate/tristearate (see also fatty acids) | AD, VG general skin protection | Fat soluble |
| Zinc stearate (see also fatty acids) | AD, VG general skin protection | Fat soluble |
| Sarcosine ester with e.g. coco, lauric, myristic acid | VG general skin protection | Fat soluble |
| Fatty alcohols (of the fatty acids mentioned as example) | VG metabolic products | Fat soluble |
| Fatty acid esters such as e.g. butyl lactate/-myristate/stearate; cetyl palmitate/-stearate/-lactate; decyl oleate; dibutyl adipate; diethyl hexyl adipate; diisopropyl adipate; dilauryl dipropionate; dioctyl palmitate/dilinoleate; ethyl acetate; glyceryl adipate/-arachidal behenate/-caprate/-caprylate/-linoleate/-oleate/-cocoate/-dihydroxy stearate/-diisopalmitate/-laurate/-undecylenate; isoamyl acetate; isobutyl stearate/-salicylate/oleate; isocetyl salicylate/-oleate; isopropyl isostearate/-lactate/-lanolate/-linoleate/-myristate/-palmitate; lauryl lactate; myristyl lactate/-myristate/-salicylate/-stearate; octyl palmitate/-stearate | Partially AO, VG: metabolic products Partially component of natural membranes | Fat soluble |
| Amino acids (in particular essential): Essential: | | |
| Lysine, valine, leucine, isoleucine, phenyl alanine, threonine, methionine, tryptophane | VG: essential cell components; threonine and leucine are described to be effective for the skin | Amphoteric |
| Proline | VG: essential component of collagen | Amphoteric |

TABLE 1-continued

| Substance/Substance Class/Extract | Effect/Protection | Solubility |
| --- | --- | --- |
| Hydroxy proline | VG: essential component of collagen | Amphoteric |
| Histidine | VG: absorption of UV light | Amphoteric |
| Arginine | VG, EH: support of skin collagen production | Amphoteric |
| Cysteine | AO, VG: antioxidant | Amphoteric |
| Various: | | |
| L-carnitine (lysine and vitamin C) | VG general skin protection | H2O soluble |
| Dimethyl amino ethanol (DMAE) | AO antioxidant | H2O soluble |
| Pycnogenol | AO, AD, VG, EH | H2O soluble |
| Urea and derivatives such as e.g. imidazolidinyl urea | VG: moisture storage | H2O soluble |
| Allantoin/glyoxylic acid diureide | VG: moisture storage | H2O soluble |
| Polyphenols/tannins: *Gallic acid and derivatives *Catechins and leuco anthocyanes retinoids (see vitamin A) | AO, AS, AM, VG, EH | |
| bisabolol | AM, VG: antiphlogistic, antimicrobial | Fat soluble |
| diols such as e.g. 1,2-pentanediol or hexanediol and derivatives such as e.g. ethyl hexanediol | VG: moisture binder | H2O soluble limited |
| diols and derivatives as mentioned above as examples with fatty acids to e.g. 1,3-butane diol ester | VG: moisture binder, spreading | H2O soluble limited |
| polyethylene glycol derivatives of different molar mass and fatty acids of e.g. coco, lauric, stearic acid | VG: reduction of the barrier function of the skin | H2O soluble limited |
| sorbitane fatty acid ester with poly ethylene glycolen of different molar mass and fatty acids to e.g. sorbitane monooleate/-laurate/tristearate/-palmitate/-trioleate | VG: reduction of the barrier function of the skin | H2O soluble limited |
| propylene glycol and derivatives with fatty acids such as e.g. oleic, lauric, myristic acid, also propylene glycol dicaprylate, -dicaprate, -dicoconate, -dipelargonate | VG: reduction of the barrier function of the skin | H2O soluble limited |
| propyl gallate | AO, AS, AM, EH | H2O soluble |
| choline | VG: general skin protection | H2O soluble |
| D-panthenol (dexpanthenol), (see also pantothenic acid) | AO, VG: skin protection/care | H2O soluble |
| Plant extracts/oils/distillate: | | |
| Green tea (camelia sinensis): extract/distillate | AO, AS, AM, VG, EH: astringent, infection prophylaxis, antimutagen, anticancerogenic | H2O soluble |
| Hamamelis (hamamelis virginiana): distillate | VG: wound-curing, antiphlogistic | Fat soluble |
| Aloe (aloe vera): gel | AO, AM, VG, EH. Wound-curing, anticrobial, antiphlogistic | H2O soluble |
| Camomile (chamomilla recutifa): oil | AO, AM, VG, EH: wound-curing, antimicrobial, antiphlogistic | Fat soluble |
| Peanut (archais hypogaea): oil | VG: skin care | Fat soluble |
| Arnica (arnica montana): oil | VG, EH: anti-inflammatory | Fat soluble |
| Almond (prunus dulcis): oil | VG: skin care | Fat soluble |
| Sunflower (helianthus annuus): oil | VG: skin care | Fat soluble |
| Jojoba (buxus chinensis): oil | VG: skin care | Fat soluble |
| Avocado (persea gratissimo): oil | VG: skin care | Fat soluble |
| Coconut (cocos nucifera): oil | VG: skin care | Fat soluble |
| Peppermint (mentha piperita): oil | VG: skin care | Fat soluble |
| Hazelnut (e.g. corylus avellana): oil | VG: skin care | Fat soluble |
| Palm seed (elaeis guineensis): oil | VG: skin care | Fat soluble |
| Rice (oryza sativa): oil | VG: skin care | Fat soluble |
| Almond (prunus amygdalus dulcis): oil | VG: skin care | Fat soluble |
| Sage (saliva officinalis): oil | AS, AM, VG, EH: germ-inhibiting, anti-inflammatory, astringent | Fat soluble |
| Yarrow (achillea milefolium): extract | AM, EM: antibiotic, anti-inflammatory | H2O soluble |

TABLE 1-continued

| Substance/Substance Class/ Extract | Effect/Protection | Solubility |
|---|---|---|
| Evening primrose (*oenethera biennis*): oil | VG: skin care | Fat soluble |
| Winter green (*gaultheria procumbens*): oil | VG, EH: antiphlogistic | Fat soluble |
| birch bark (*betula alba*): distillate | AS, AM, VG, EH: antiphlogistic | Fat soluble |
| marigold (*calendula officinalis*): oil | VG, EH: supports epithelium formation | Fat soluble |

AO: anti-oxidative (protection from radicals)
AS: astringent, solidifying, mechanically stabilizing ("tanning")
AM: anti-microbial (protection from opportunistic germs and protection from toxic metabolic products)
VG: (re)vitalizing, maintaining health, general skin protection
EH: anti-inflammatory action Any conventional production methods known by the person skilled in the art can be used to produce the skin-care product-containing, super-absorbing polymer material, which is suited for the inventive suction body component.

With regard to production and selection of the super-absorbing polymer material which can be used in the core, reference is made to the literature known by the person skilled in the art, e.g. DE 4020780, EP 1169372 B1, US Re. 32,649, EP 0752892 B1, EP 0744967 B1 and EP 0304319 B1. It is preferably a partially neutralized polyacrylic acid polymer, the surface of which is subsequently cross-linked to increase the gel stability.

If, in a preferred embodiment, the core of the super-absorbing polymer material also comprises a skin care product, the skin care product may be connected to the core of the super-absorbing material in various ways during production of the core of the super-absorbing material. These include e.g. the possibility of mixing the dry skin care product a) with the finished, subsequently cross-linked core of the super-absorbing material, b) mixing it with the not yet cross-linked core of the super-absorbing material, c) mixing it with the polymerized but not yet dried gel or d) mixing before or during polymerization of the core of the super-absorbing material. It may be advantageous to add a liquid, in particular, an aqueous component before or after mixing to improve bonding between the skin care product and the core of the super-absorbing material.

The skin care product may also be connected to the core of the super-absorbing material or be mixed with the coating agent not in a dry, but in a wet or moist state. Towards this end, it may be previously dissolved, mixed or dispersed in suitable liquid or semi-liquid materials, such as e.g. aqueous or organic solvents.

Conventional devices may be used for mixing.

Any material suited to reduce the absorption rate of the super-absorbing polymer material, in particular, substances which dissolve in an aqueous liquid or swell, such as natural or synthetic celluloses or lignocelluloses, cellulose derivatives such as e.g. methyl celluloses, carboxy methyl celluloses, ethyl celluloses, hydroxy propyl celluloses, cellulose acetates, may be used as coating agent to form at least part of the outer surface of the core of the super-absorbing material and comprising a skin care product as a further component. It is also possible to use several, i.e. at least two different coating agents.

Methods for coating the cores of super-absorbing polymer materials are known in the art. WO 00/62825 and WO 02/36663 disclose coating methods which are suited to the present invention. Reference is hereby made to the full disclosure of the above-mentioned patent applications which are hereby incorporated by reference. The preferably powdery coating agent is initially dry mixed with the core of the likewise powdery super-absorbing polymer material, and subsequently wetted with water and then mixed again.

To provide at least the coating agent with a skin care product in accordance with the invention, the skin care product can be connected to the coating agent in different production steps of coating the core of the super-absorbing material or during production of the coating agent itself. These include e.g. mixing the dry skin care product a) with the finished super-absorbing material having the coating agent, b) with the pre-fabricated coating agent prior to coating the core of the super-absorbing material to apply a coating agent that already contains a skin care product, c) mixing the skin care product with the coating agent before or during production of the coating agent and subsequently applying the coating agent containing the skin care product. It may also be advantageous to add a liquid, in particular, an aqueous component, before or after mixing to improve the connection between the skin care product and the coating agent.

Instead of using a dry skin care product, the skin care product may previously be dissolved, mixed or dispersed in suitable liquid or semi-liquid media such as e.g. aqueous or organic solvents.

A binder component may also be used which has an adhesion-promoting effect between the coating agent and the skin care product and/or the core of the super-absorbing polymer material.

An amount of skin care product of preferably 0.001-100%, in particular 0.1 to 10%, and preferably 0.5 to 5% relative to the overall weight of the super-absorbing polymer material is regarded as advantageous.

The particle size of the super-absorbing material provided as super-absorbing polymer material core is usually preferably between 10 and 1000 μm.

If the skin care product is connected to the coating agent and preferably to the absorbing core of the super-absorbing polymer material in a dry state, the skin care product is preferably used in powder form, in particular, having a particle size between 5 and 900 μm.

The particle size of the coated super-absorbing polymer material comprising the skin care product is also usually preferably between 10 and 1000 μm.

The grain size of the coated super-absorbing polymer material comprising the skin care product may be set to the preferred range after coating.

In accordance with an advantageous embodiment of the invention, the carrier material of the inventive suction body component comprises natural or synthetic fibers such as cellulose fibers, thermoplastic fibers e.g. of the group of polyolefines and/or foamed material and/or a thermoplastic preferably extruded synthetic matrix.

The carrier material may form a matrix so that the super-absorbing polymer material is preferably homogeneously bound in the carrier material.

A layer-forming configuration is also feasible, wherein the super-absorbing polymer material is disposed on one of the large surfaces of the carrier material. In this case, the carrier material comprises, in particular, a tissue, a non-woven material and/or a foil.

In a particularly advantageous manner, the inventive suction body component is used within an absorbing hygiene product. In this case, the hygiene product preferably comprises a back sheet facing away from the body which is liquid-proof at least in sections and which preferably breathes, and/or a top sheet facing the body which is liquid-proof, at least in sections. The top and back sheets thereby surround the inventive suction body component.

Further suction body layers may preferably be disposed above or below the inventive suction body component to improve, in particular, the distribution and/or storage of body excretions such as urine, blood or stool.

In addition to the super-absorbing polymer material containing skin care products, the inventive suction body component may also comprise super-absorbing polymer materials without skin care products (in particular, even without a coating agent) which are capable of quickly binding part of the produced liquid in certain applications and which are characterized in that very large amounts of liquid must be absorbed by the suction body component within a very short period.

The invention also concerns use of a suction body component for application of skin care products onto human skin, comprising a carrier material and a super-absorbing polymer material, wherein the super-absorbing polymer material comprises a core with an outer surface, and at least part of the outer surface of this core comprises a coating agent which can reduce the absorption rate of the super-absorbing polymer material, wherein the coating agent of the super-absorbing polymer material comprises a skin care product.

The invention also concerns use of a suction body component for producing a product which improves the health of human skin, comprising a carrier material and a super-absorbing polymer material, wherein the super-absorbing polymer material comprises a core with an outer surface, at least part of the outer surface of this core comprising a coating agent which can reduce the absorption rate of the super-absorbing polymer material, wherein the coating agent of the super-absorbing polymer material comprises a skin care product.

Further features, details and advantages of the invention can be extracted from the drawing and the following description of preferred embodiments of the invention.

DESCRIPTION OF THE PREFERRED EMBODIMENT

Figure 1:
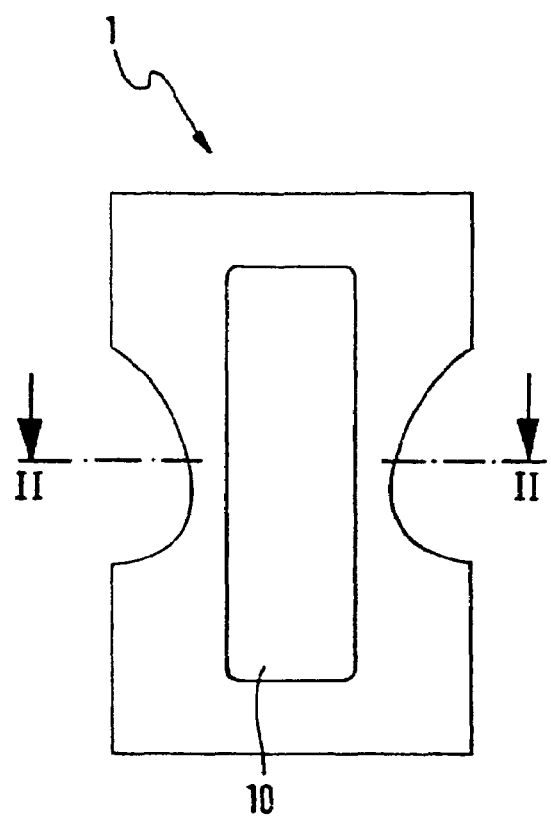
FIG. 1 shows a schematic top view of a hygiene product for single use, with the inventive suction body component.
Figure 2:
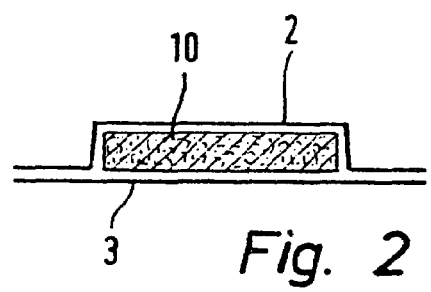
FIG. 2 shows a sectional view of the hygiene product of FIG. 1 according to the sectional plane II-II of FIG. 1.

FIGS. 1 and 2 show a single-use diaper 1 with an inventive suction body component 10. The suction body component 10 is covered, proximate to the body, by a liquid-permeable top sheet 2 which, together with the liquid-proof, breathable back sheet 3 positioned remote from the body, surrounds the suction body component 10 in a sandwich-like fashion. The single-use diaper can comprise further components (not shown) such as e.g. closure elements, elastic leg and/or waist ends and terminating barriers extending in a longitudinal and/or transverse direction.

Figure 3:
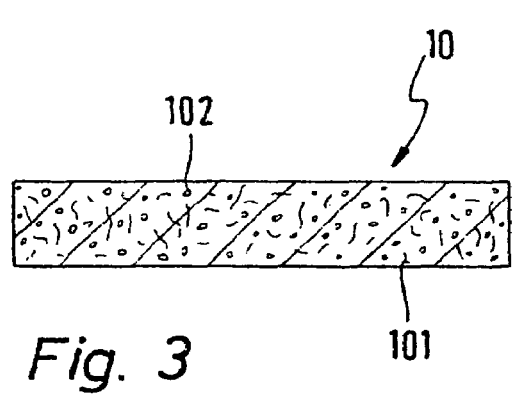
FIG. 3 shows an enlarged sectional view of the inventive suction body component only.

FIG. 3 shows an enlarged view of the inventive suction body component 10. The suction body component 10 comprises a matrix-forming fiber material 101 which, in the present case, consists essentially of fluffed cellulose fiber material.

The super-absorbing polymer particles 102 are substantially homogeneously mixed with the cellulose fiber material 101. The fraction of the super-absorbing polymer particles 102 relative to the overall weight of the inventive suction body component 10 is 15 to 85%, preferably 30 to 70%.

Figure 4:
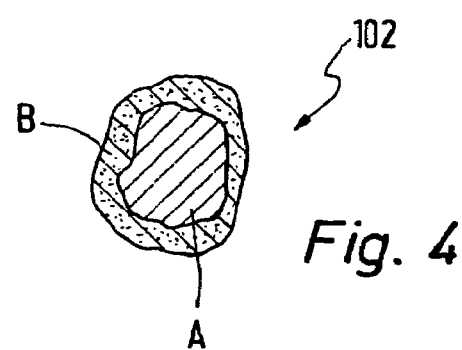
FIG. 4 shows a sectional view through a particle of the super-absorbing polymer material of the inventive suction body component.

FIG. 4 shows an enlarged view of a section through a preferred super-absorbing polymer particle 102. The polymer particle 102 has a grain size of 10 to 1000 μm, preferably 100 to 800 μm, and has a core A of super-absorbing polymer material. The super-absorbing polymer material of the core A comprises 2% (weight percent) of dried green tea extract as a skin care product.

The outer surface of the core A of the super-absorbing polymer particles 102 is essentially completely coated with Na-carboxy methyl cellulose which comprises 2% (weight percent) of the dried green tea extract as skin care product.

I claim:

1. A suction body component for long-term storage of body liquids in absorbing, skin-friendly, single-use products, the suction body component comprising:
    a carrier material;
    a particulate, super-absorbing polymer material, said particulate polymer material comprising a plurality of super-absorbing polymer particles;
    a coating deposited on individual outer surfaces of individual said super-absorbing polymer particles to coat said outer surfaces of said individual polymer particles for reducing a respective individual absorption rate thereof, said coating having a cellulose material selected from the group consisting of natural cellulose, synthetic cellulose, lignocellulose, cellulose derivatives, methyl cellulose, carboxy methyl cellulose, ethyl cellulose, hydroxy propyl cellulose, and cellulose acetate; and
    one or more skin care products, wherein at least 50% of said skin care products are disposed within said super-absorbing polymer particles and a rest percentage of said skin care products is disposed in said coating, said rest percentage of said skin care products in said coating comprising a plant component, a plant extract, plant oil, or plant distillate.

2. The suction body component of claim 1, wherein at least 65% of said skin care products are disposed within said super-absorbing polymer particles.

3. The suction body component of claim 1, wherein said skin care products are water-soluble.

4. The suction body component of claim 1, wherein said skin care products comprise a vitamin.

5. The suction body component of claim 1, wherein said skin care products comprise an organic acid.

6. The suction body component of claim 1, wherein said skin care products comprise an amino acid.

7. The suction body component of claim 1, wherein said carrier material comprises cellulose fibers, synthetic fibers, a foamed material, a porous matrix, and/or a thermoplastic synthetic matrix.

8. The suction body component of claim 1, wherein said carrier material forms a matrix and said particulate super-absorbing polymer particles are homogeneously bound in said carrier material or in sections thereof.

9. The suction body component of claim 1, wherein said super-absorbing polymer particles are disposed over a large surface area of said carrier material to form a layer.

10. An absorbing single-use product comprising the suction body component of claim 1, wherein the product comprises a top sheet facing a users body and a back sheet facing away from the user's body, said top and said back sheets surrounding and sandwiching the suction body component.

11. An absorbing single-use product comprising the suction body component of claim 1, wherein at least one further liquid-permeable layer is disposed above the suction body component at a user's body side.

12. Use of the suction body component of claim 1, for disposing skin care products onto human skin.

13. Use of the suction body component of claim 1, for producing a product to improve health of human skin.

* * * * *